United States Patent [19]

Subotics et al.

[11] Patent Number: 5,077,009

[45] Date of Patent: Dec. 31, 1991

[54] METHOD FOR PRESERVING PERISHABLE ORGANIC MATTER

[75] Inventors: Gyula Subotics; Gyuláné Subotics, both of Budapest, Hungary

[73] Assignee: Zelsa Patentverwertung GmbH, Vienna, Austria

[21] Appl. No.: 356,880

[22] Filed: May 24, 1989

[30] Foreign Application Priority Data

Jun. 8, 1988 [HU] Hungary .............................. 2970/88

[51] Int. Cl.⁵ .......................... F25D 17/06; A23B 4/06
[52] U.S. Cl. ........................................ 422/40; 62/78; 422/1; 426/418; 426/419; 426/486
[58] Field of Search ...................... 422/1, 40; 426/418, 426/419, 486; 62/78

[56] References Cited

U.S. PATENT DOCUMENTS

3,958,028 5/1976 Burg .
4,246,835 1/1981 Knutrud .

Primary Examiner—Jill Johnston
Attorney, Agent, or Firm—Schweitzer Cornman & Gross

[57] ABSTRACT

The invention relates to a method and an equipment for the preservation of vegetables, meat or other organic substances. The essential feature of the method proposed by the invention consists of placing the goods to be preserved into a hermetically sealed chamber (I, II), then varying the composition of the gases bound by the cell material of products. The essential feature of the equipment complying with the invention consists of placing the goods to be preserved into a hermetically sealed chamber (I, II), where the chamber (I, II) is connected with some means, advantageously with a gas pump, for varying the pressure within said chamber, or providing said chamber (I, II) with at least one hermetically sealed, movable wall for varying the volume of said chamber, further connecting the latter with a cooling circuit for providing the cooling of the chamber (I, II).

6 Claims, 11 Drawing Sheets

METHOD FOR PRESERVING PERISHABLE ORGANIC MATTER

FIELD OF THE INVENTION

The invention relates to a method and equipment for preservation of vegetables, meat or other organic materials.

As is known, most kinds of goods of materials of vegetable or animal origin can be preserved for longest periods of time in their frozen state.

One serious drawback of preservation by freezing is associated with the water content of the product freezing out of the aqueous solutions of salts, sugars, etc. contained in the cells, and the cell-walls are pierced by the growing ice crystals. When the frozen product is thawed later, the cell-walls become pervious to water, and the fibres of the product get disintegrated. After thawing the quality of the preserved goods will, hence, differ from their quality previous the freezing, e.g. fruits, green-stuff and other vegetables become squashy, loose their original flavour and colour, meat gives off juice. Therefore, a product after having frozen once must not be allowed to freeze again after thawing, neither be allowed to thaw partially and then to freeze slowly again.

With quick-freezing, the water in the cells forms tiny crystals that exert a less damaging effect on the cell-walls, but total elimination of injury to the cells cannot be accomplished either in that case, for the simple reason of volume increase of water taking place in the course of freezing, causing the weak cell-walls to burst under the piercing effect of the tiny ice crystals. Also tomatoes, strawberries, bananas, mushrooms etc. get limp, and change their colour and flavour when taken out of the quick-freezer. There are products, e.g. whole eggs, onion, radish, lettuce, etc. that are not at all suitable for being frozen.

A further drawback of quick-freezing is the rather long time required to thaw out the products before consumption.

Preservation methods applying high temperatures or conserving agents also show several disadvantages. They change the taste, colour and consistency of preserved products. While loosing also their vitamine content, at the same time the preserving agents are in many cases deleterious to the health. Again a further disadvantage of the known methods is the complexity and costliness of their industrial realization.

DESCRIPTION OF THE INVENTION

Aim of the invention is to eliminate the drawbacks of known methods by introducing a preservation method based on continuous modification of the composition of gases bonded in the cell material of products to be preserved, impeding thereby the multiplication of microorganisms.

A further aim of the invention is to provide an equipment suitable for accomplishing said method.

The invention is based on the recognition that by continuously modifying at a certain temperature the composition of gases bonded in the material of certain cells, e.g. bacteria, viruses, etc., their multiplication can be reduced or even fully prevented.

On the other hand, the concentration pertaining to the saturation point of a gas dissolved in liquids—i.e. the solubility of a gas—is proportional to the pressure (p) and increases with reducing temperature.

The essential feature of the method according to the invention consists of placing into a closed space the product to be preserved, then of changing the composition of gases bonded by the cell material of said product.

It is of advantage to change the composition of gases bonded in the cell material of the products to be preserved by modifying the pressure and/or temperature of gases, preferably those of the air, filling up said closed space. It is purposeful to change cyclically the temperature of the gases filling up the closed space between $-2°$ C. and $+2°$ C., while the amount of cyclical change of pressure is below 8 kPa and its frequency is at least $0.1 \text{ s}^{-1}$.

Another way of proceeding in accordance with the invention is to vary the pressure prevailing in the closed space so as to increase the frequency of pressure variation with decreasing temperature.

The essential feature of equipment complying with the invention consists of accommodating the product to be preserved in a hermetically sealed chamber, where the equipment serving for varying the pressure within said chamber is preferably coupled with a gas pump, or the chamber is provided with at least one displaceable wall ensuring the possibility of changing the volume of said chamber and serving for hermetically sealing the latter, where said chamber is in connection with a basic cooling circuit ensuring the cooling of the chamber.

It is of advantage to provide the equipment with two chambers communicating with each other through a rotary gas pump, where a check valve is built in the wall between the two chambers.

It is preferable to have a thermostat installed for sensing the temperature in the chambers, the thermostats being coupled with the closed control circuit provided for regulating the changing pressures of the chambers and with the closed control circuit for regulating the chamber temperatures.

The equipment is preferable of portable design, where the closed control circuit is coupled with a d.c. motor supplied from a storage battery.

It is of advantage to connect the closed control circuit with a motor fed from a battery or from the mains.

The goods to be preserved are placed in a closable container or room, in which the pressure of the air—at the desired temperature—can be changed continuously.

In liquids—namely in the material of cells—the dissolution of gases filling up the sealed space containing the goods to be preserved can be further enhanced by continuously changing also the temperature of said gases simultaneously with continuously varying their pressure.

According to a possible embodiment of the equipment, the pressure of gases filling up the sealed space is preferably changed by means of a reciprocating or rotary gas pump, and using the heat pump cycle for producing the required temperature changes.

According to another possible embodiment, the permanent pressure changes of gases filling up the inside of larger sealed storage spaces can be achieved e.g. by continuously moving a partition wall tiltable in both directions around an axis, and hermetically sealed along its periphery by a flexible sealing element.

Pulsation of pressure within the sealed storage space of gases offers advantages also from the respect of preventing a freezing-out of water contained by the cells of products to be preserved even when the temperature drops below 0° C. Since, by means of adjusting the temperature and pressure conditions correspondingly, formation of ice crystals can fully be prevented, so the cells of the products can be kept intact in their original state during the entire process of the preservation.

Examples of the invention represented by a number of embodiments are described closer with reference to the attached drawings, where.

Figure 1:
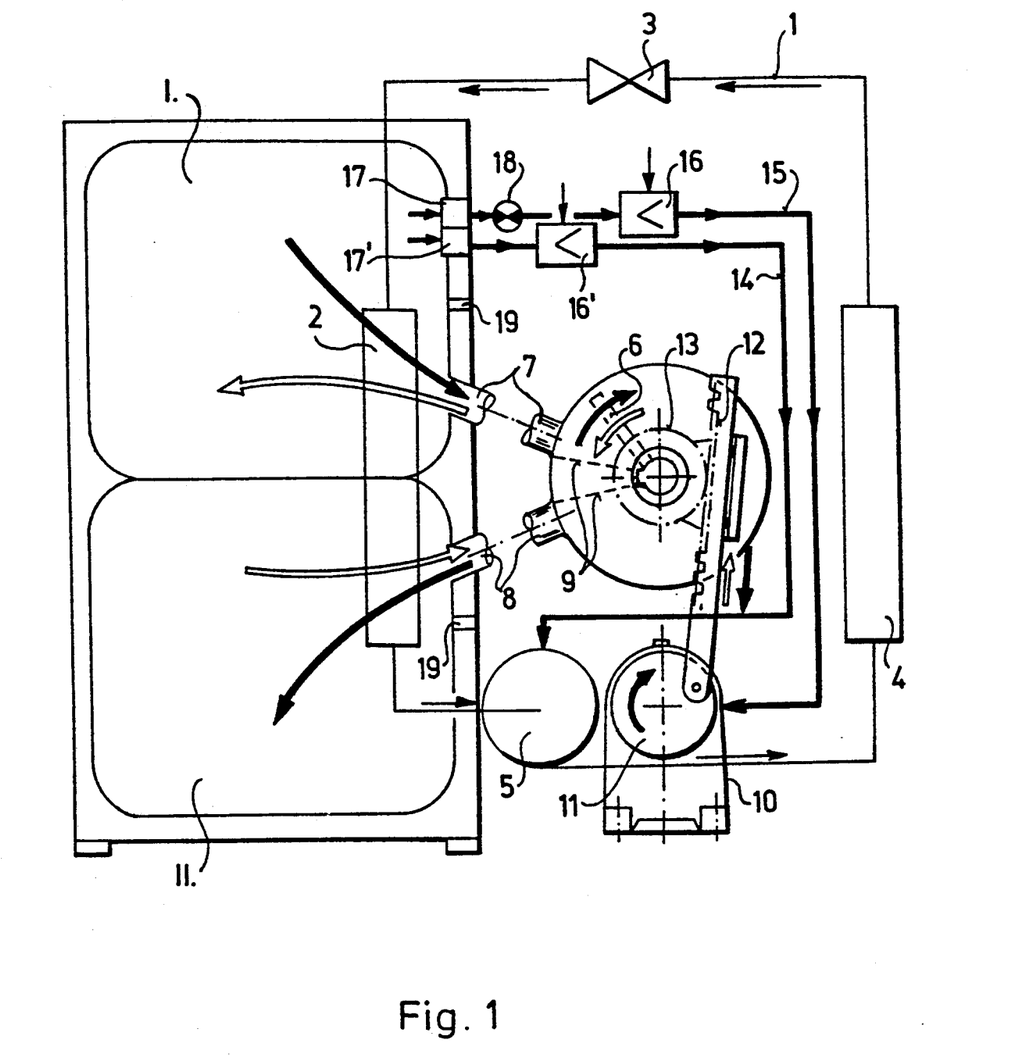
FIG. 1 is showing the equipment suitable for varying continuously the pressure and temperature of gases filling up the sealed space of the storing unit consisting of two chambers for preserving goods by means of the method complying with the invention.

Hence, the principle of operation of the equipment serving for preservation of goods by means of the method complying with the invention is represented in FIG. 1.

The equipment shown in FIG. 1 comprises two hermetically sealed chambers I and II for receiving the good to be preserved, where said two chambers I and II communicate with each other through a rotary gas pump connected with one of its stubs 7, to chamber I and with its other stub 8 to chamber II.

Rotary piston 6 of the rotary gas pump is mounted on the shaft common with gear 13. Gear 13 meshes with rack 12 attached with one end to crank disk 11 through a bearing. Crank disk 11 is coupled with a crank drive integrally built with motor 10. In the casing of the rotary gas pump the suction chamber is confined by insertions 9 placed between stubs 7, 8. The minimum gas pressure in chambers I, II can be set by means of check valves 19 mounted into the wall of each chamber I and II. The two chambers I and II are provided with a temperature regulating cooling circuit known from refrigeration technology, comprising evaporator 2 arranged in chambers I and II and outside chambers I and II—looking in direction 1 of the full cycle of the working medium-compressor 5, condenser 4 and expansion valve 3 are inserted.

In chambers I and II the changing of pressure is ensured by closed control circuit 15, while changing of temperature by closed control circuit 14.

The closed control circuit 14 includes thermostat 17', amplifier 16' (when required), and compressor 5 whereas closed control circuit 15 comprises thermostat 17, pilot lamp 18, amplifier 16 (when requpred), and motor 10.

By rotating the rotary piston 6 a fluctuation in the pressure of chambers I and II can be ensured, and the cyclical nature of this fluctuation is achieved by periodic reversal of the sense of rotations of rotary piston 6.

In one sense of rotation of rotary piston 6 stub 7 acts as suction stub and stub 8 as pressure stub connection, whereas in the other sense of rotation, stub 7 is the pressure stub and stub 8 the suction stub.

Figure 2:
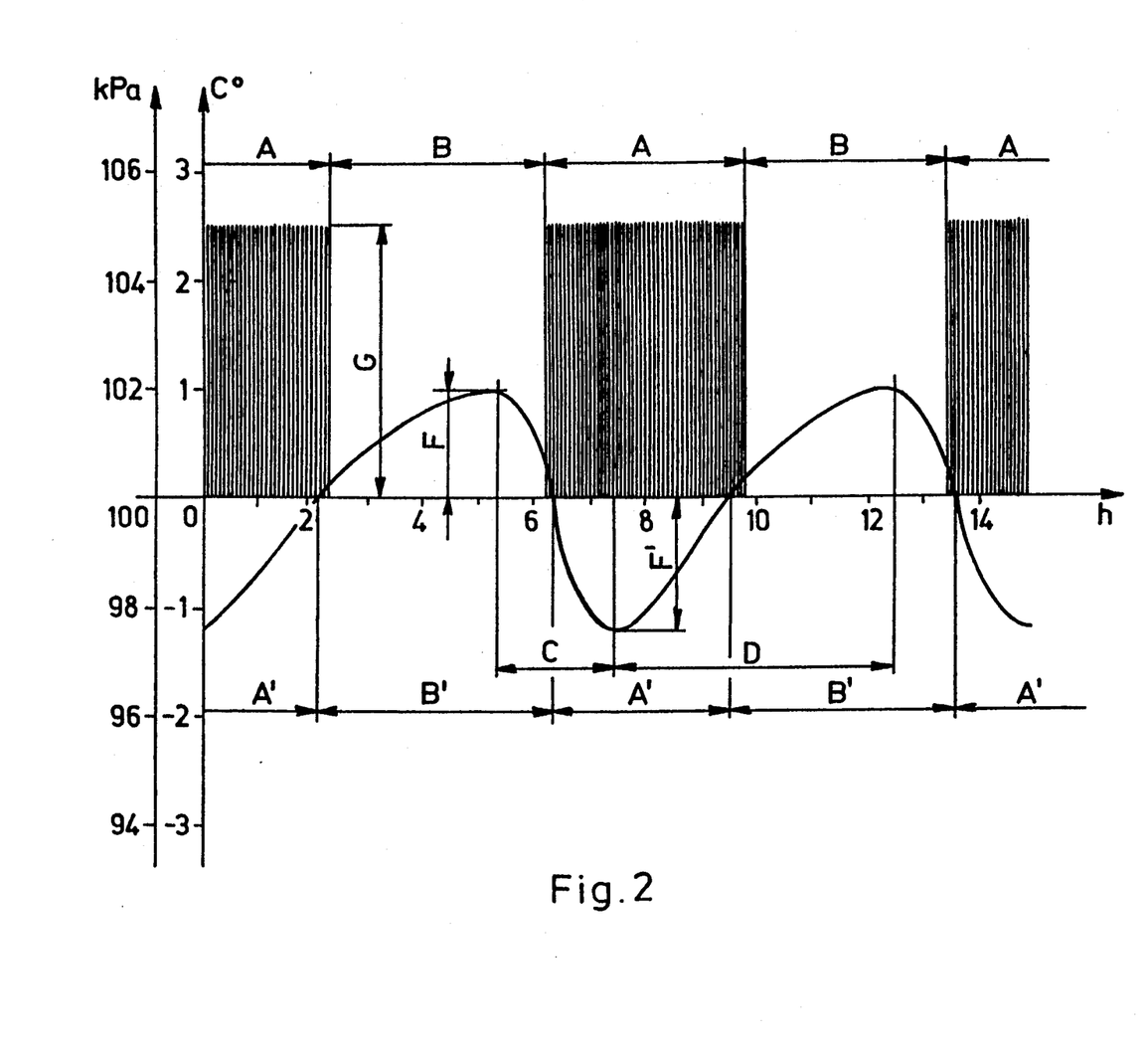
FIGS. 2, 3, 4, 5, 6, 7 represent different curves showing possible variations of temperature and pressure of gases filling up the storage space, in the function of time.

FIG. 2 illustrates that kind of possible changes of temperature and pressure of the gases filling up the storage space, where continuous periodic temperature variations take place in the interval 5 between the highest +F and the lowest −F' levels, so that the temperature is above 0° C. for a period of B' and below 0° C. for a period of A'.

Cooling from the highest temperature +F to the lowest temperature −F' takes place within time period C, then for heating from the lowest temperature −F', to the highest temperature +F the time period D is needed. While the temperature changes are taking place, during period of A which incorporates interval A, i.e. with a short overlap of time, but essentially from that instant on when the temperature of gases drops below 0° C., the fluctuating pressure change of the gases starts and goes on continuously during the entire time period A in the interval G being above the atmospheric pressure. During period B the fluctuating pressure variations can cease, so that at such times the pressure of gases in storage chambers I, II may be equal to the external (atmospheric) pressure. In the case when the temperature of the storage space does not drop below −1.5° C., the pressure variation of the gases lies preferably between 100 and 105 kPa, and the frequency of the fluctuation is expediently $v \approx 1s^{-1}$.

Figure 3:
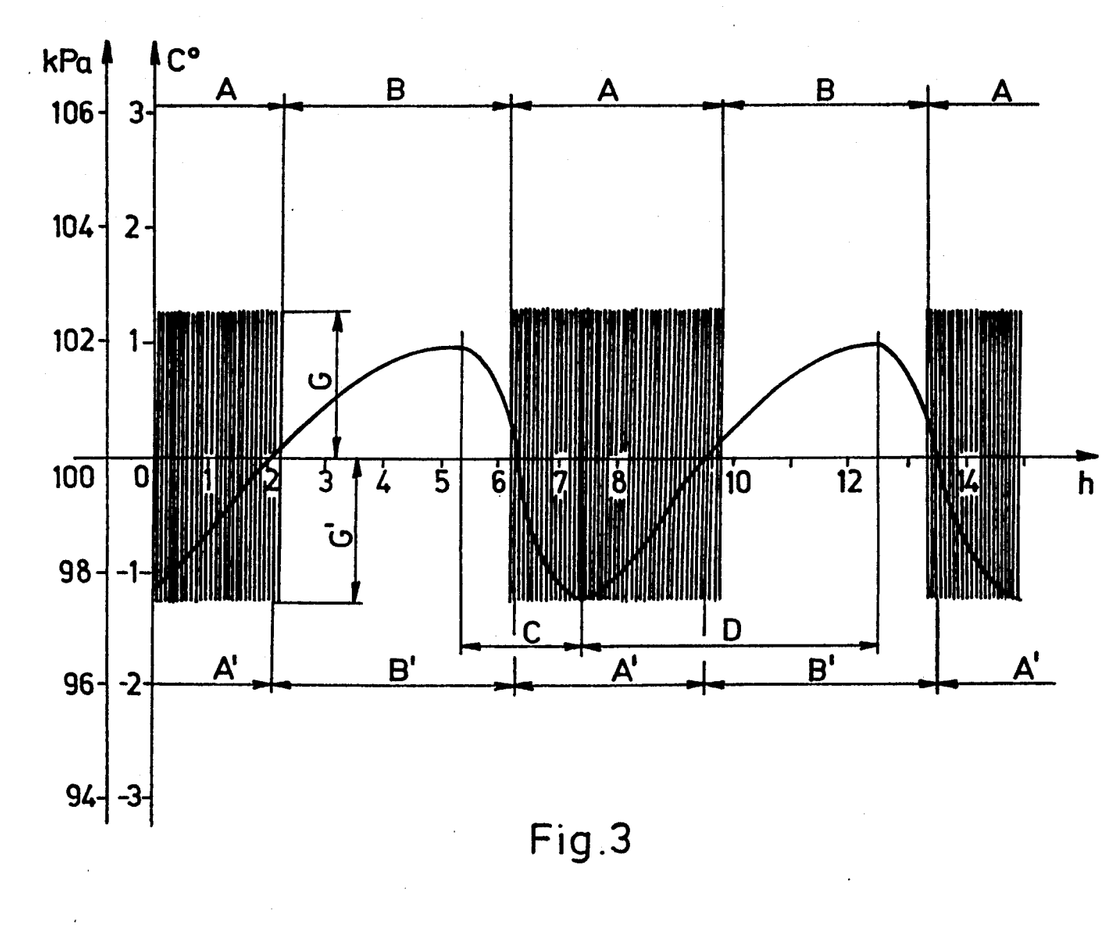

According to FIG. 3 the temperature change of the storing space in the function of time is equal to that shown in FIG. 2. Differences can be seen only in the minimum and maximum values of the pressure variation of the gases.

In the case illustrated in FIG. 3, the pressure of gases is changing in the range of 97.5 to 102.5 kPa. The frequency pulsation is $v \approx 1s^{-1}$ also in this case.

In the mode of operation according to FIG. 3, the aqueous solution present in the cells of products subject to the preservation treatment tend to migrate outside the cell wall unter the suction effect acting on the cells, that may lead to a fluid loss of certain degree of the cells. Therefore, with the preservation process it is essential to adjust pressure ranges G and G' properly in the range G of overpressures by means of check valve 19 shown in FIG. 1.

Figure 4:
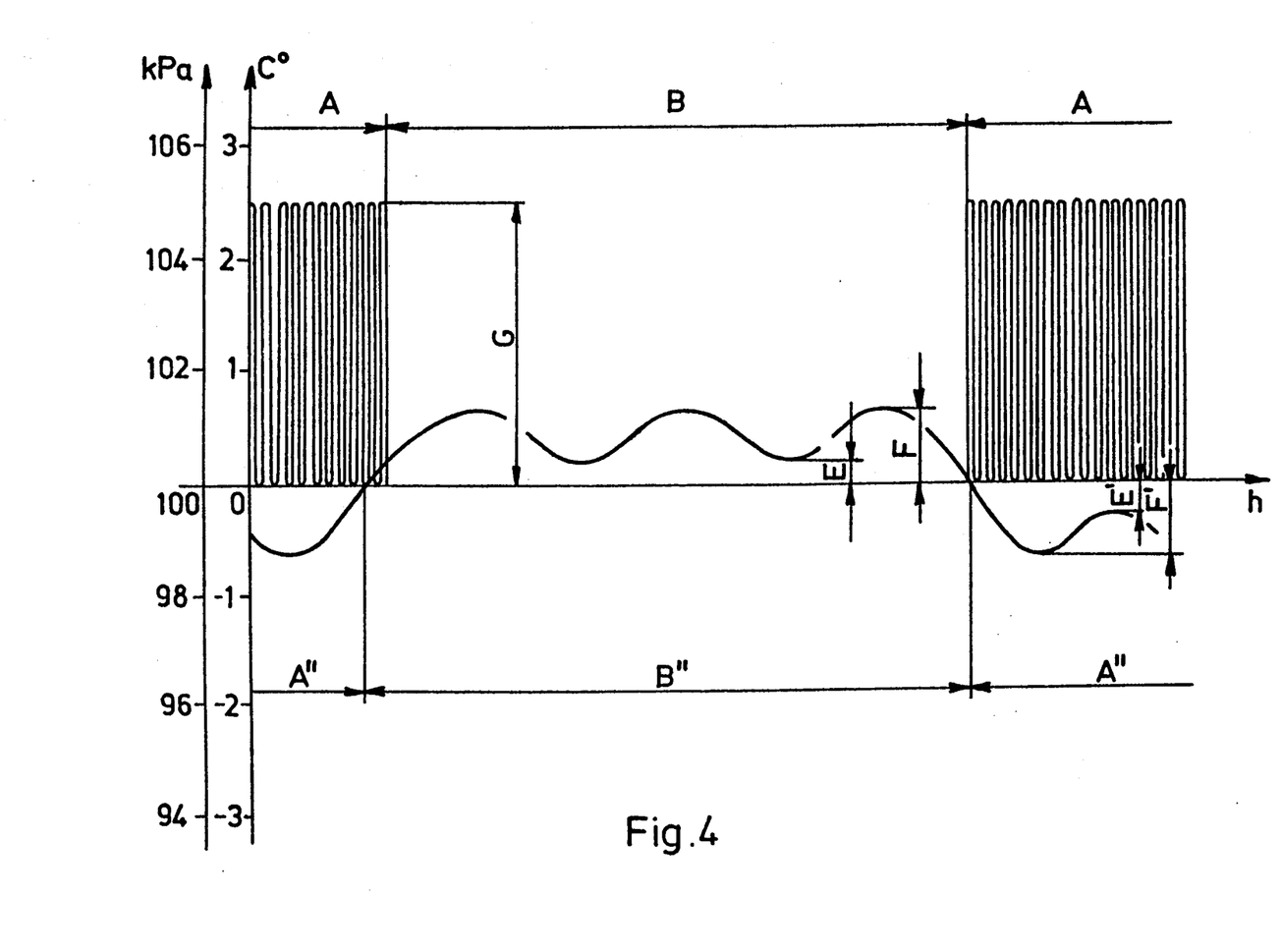

In the mode of operation shown in FIG. 4 the temperature change of the shortage space is controlled so that above 0° C. it is kept between +0.2° and 0.8° C., time period B'' should be longer than B', further if the operating temperature range below 0° C. lies between −0.2° and −0.8° C. and time period A'' should be longer than A'. Also the pressure conditions of the storage space automatically controlled in this way by thermostats can be adjusted to more suitable parameters either so that the overpressure interval G be <5 kPa, or so that the frequency be ν<1.

Thereby, preservation can be achieved with lower energy consumption without impairing the quality of products in thee course of the preservation process.

Figure 5:
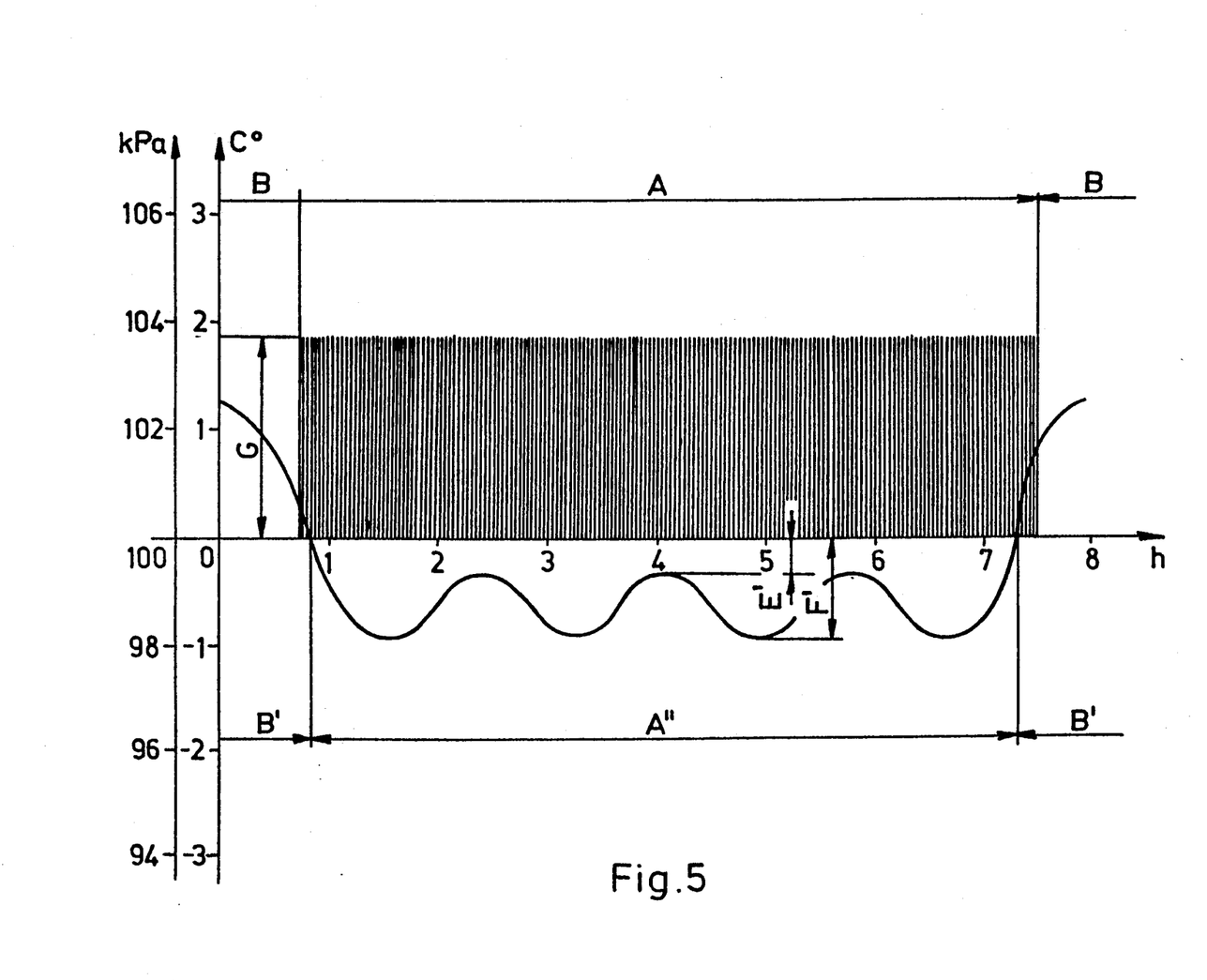

In the mode of operation shown in FIG. 5 preservation takes place exclusively in the temperature range below 0° C., otherwise under the conditions of FIG. 4. In the case complying with FIG. 5, periods B' indicate the switching-on of cooling at the beginning of the preservation process and the switching-off of cooling at the end of the process respectively. This mode of operation is preferable mainly for preservation of meat.

Figure 6:
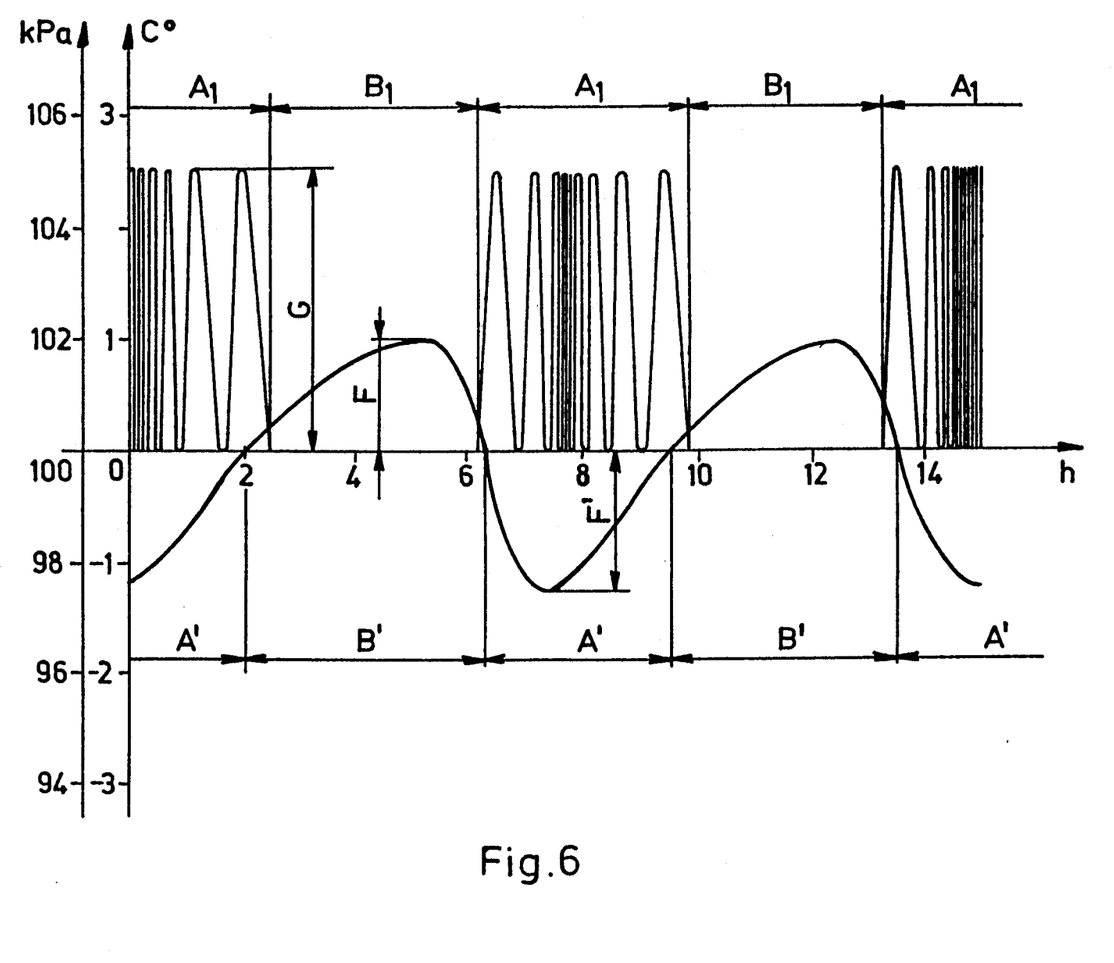
Figure 7:
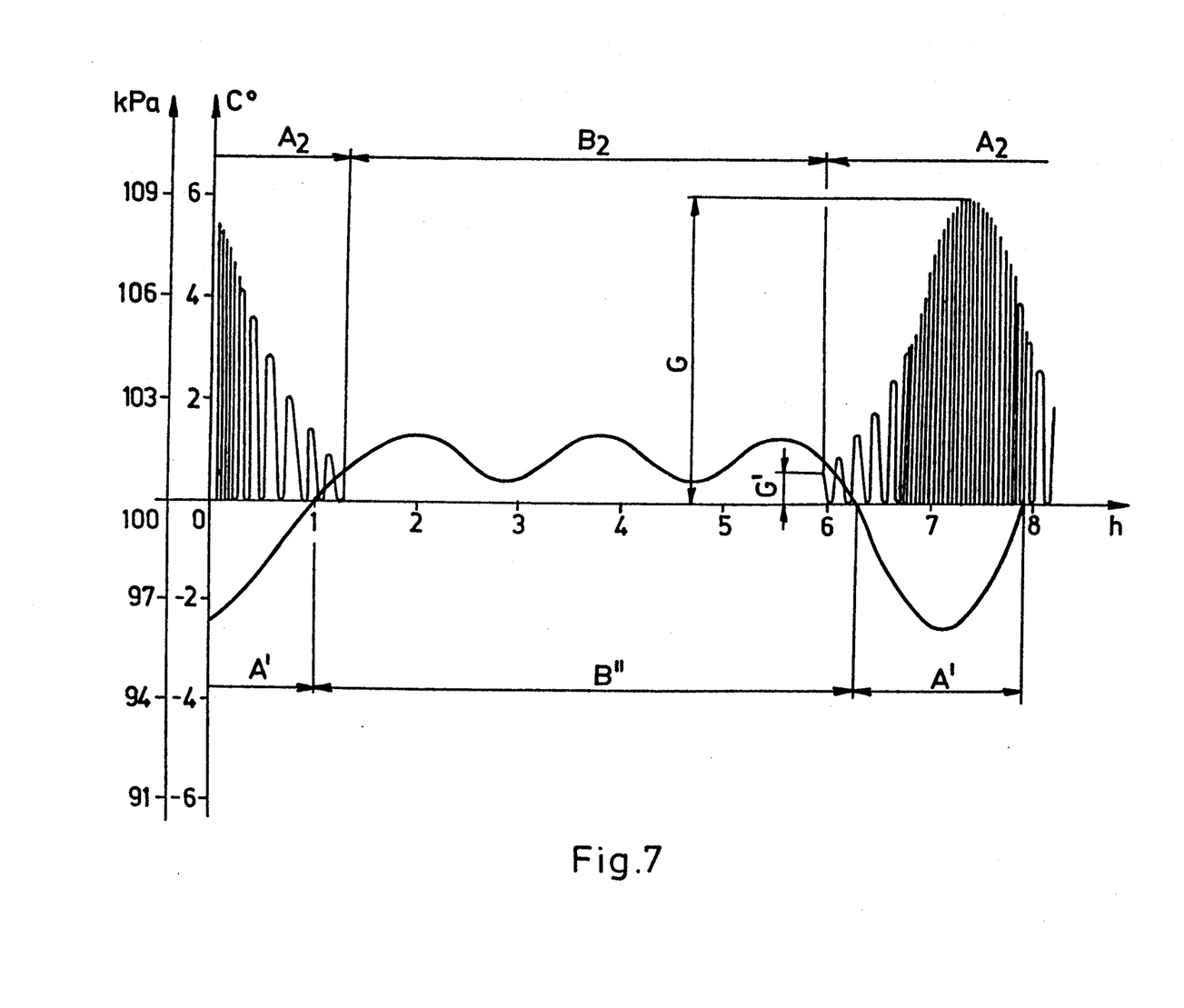

By the mode of operation of FIG. 6 further energy may be spared by increasing the frequency of pressure fluctuation with decreasing temperatures, or by simultaneously applying the method of increasing the frequency and increasing amplitude G of overpressure fluctuations, as shown in FIG. 7.

Figure 8:
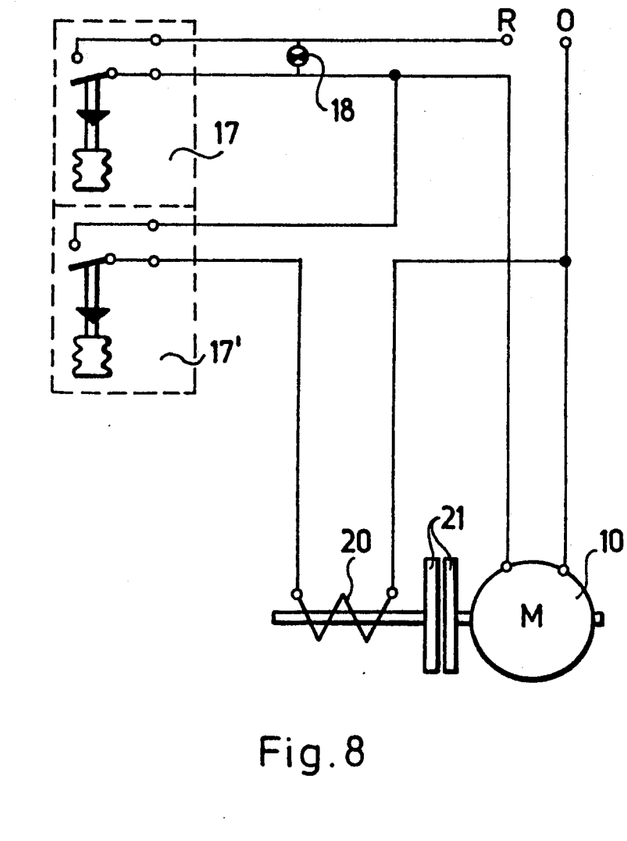
FIG. 8 is the electrical circuit diagram of a mains-supplied and automatically controlled equipment of smaller output for preservation of goods using the method complying with the invention

FIG. 8 is the electrical circuit arrangement of an automatically controlled equipment of lower output, for preservation of goods by the methods complying with the invention.

The rotary gas pump is switched on and off by means of thermostat 17 comparing the set value of the temperature with the measured value in the preservation space. The rotary-piston gas pump is driven by motor 10 integrally built with a crank drive through an interposed transmission gear.

Also on the basis of the temperature set, the thermostat 17' controls through contactor 20 the engagement and disengagement of clutch 21 causing the starting of compressor 5 of the cooling circuit. The switched-on state of the gas pump is indicated ba pilot lamp 18.

Figure 9:
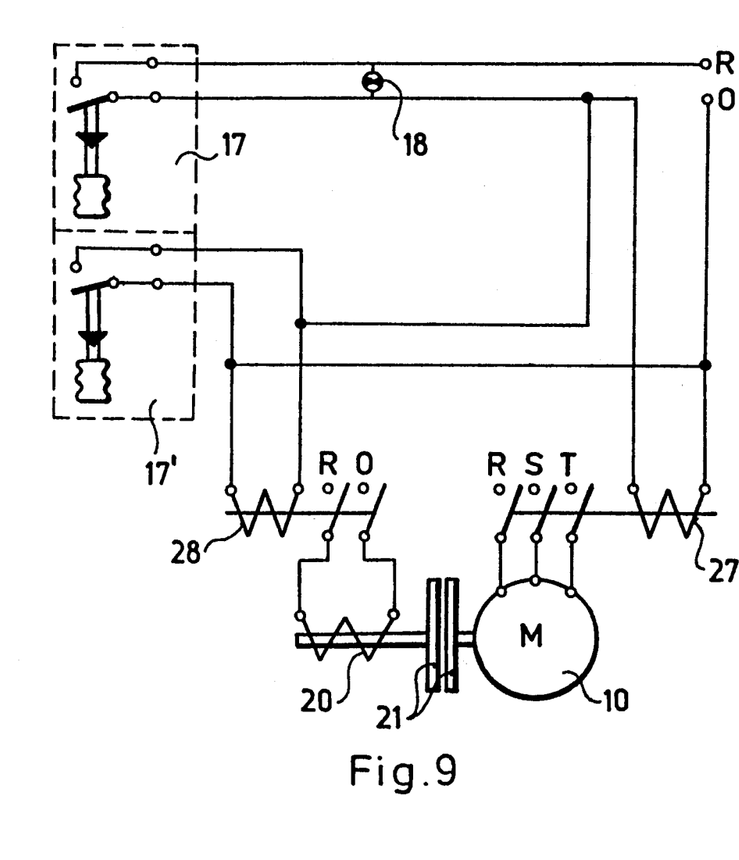
FIG. 9 is the electrical circuit diagram of a mains-supplied and automatically controlled equipment of higher output for preservation of goods using the method complying with the invention

FIG. 9 illustrates the circuit diagram of an automatically regulated, mains-operated equipment of higher output, otherwise being similar to that of FIG. 8, serving for the preservation of goods in accordance with the invention, where contactor 20 of clutch 21 operating electric motor 10 and compressor 5 respectively, through the intervention of contactors 27, 28 of smaller current consumption, is controlled by thermostats 17 and 17' respectively.

Figure 10:
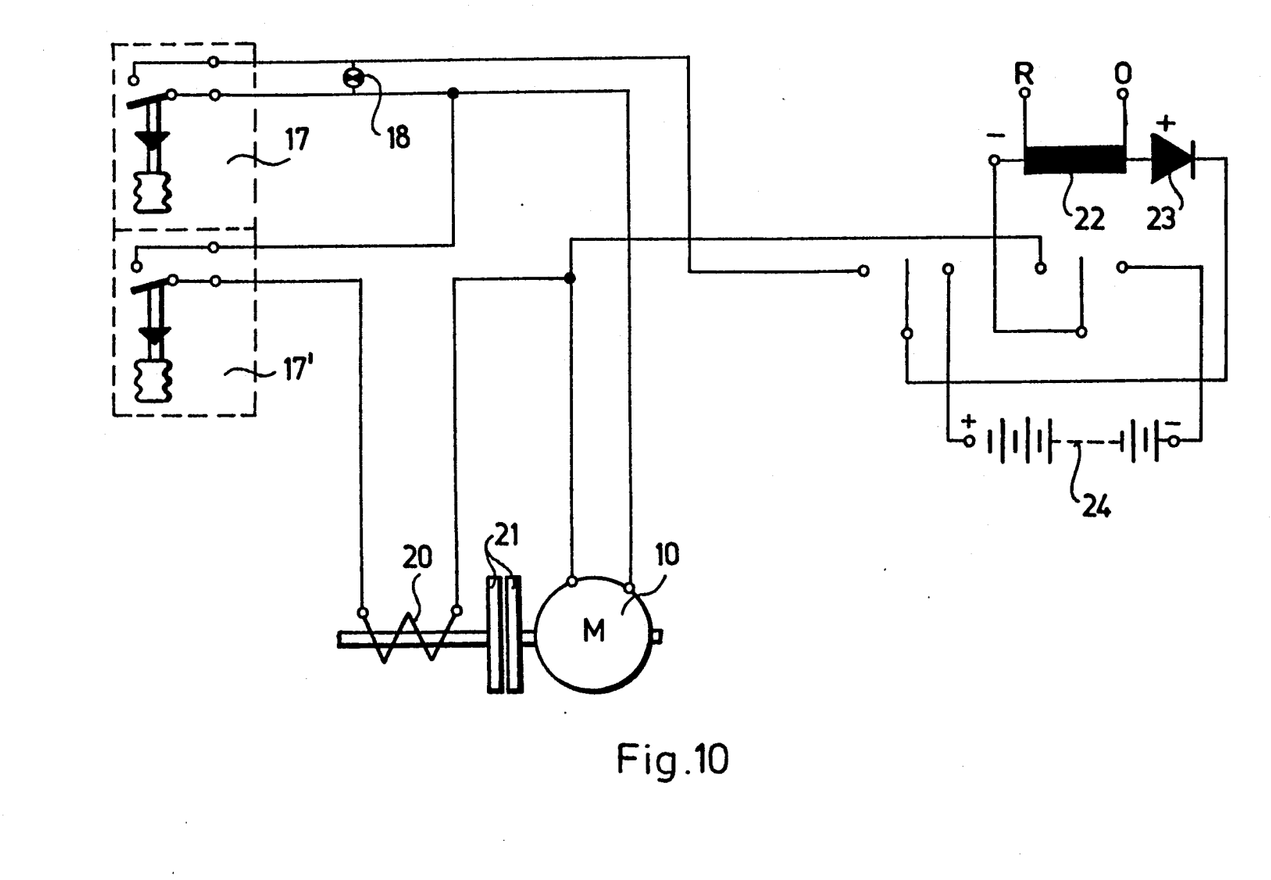
FIG. 10 is the electrical circuit diagram of an equipment for preservation of goods using the method complying with the invention, suitable both for mains and battery operation.

FIG. 10 is an improved embodiment of the circuit arrangement of FIG. 8, where the equipment is driven by a D.C. motor fed from battery 24, with the possibility of recharging said battery from the mains through transformer 22 and rectifier 23. This embodiment can be used for operation of equipment built in cars and realizing the preserving method of the invention, as you have the possibility to recharge the batteries from the mains when the equipment out of work.

These embodiments, e.g. the mobile construction of the preserving equipment preferably can be used in sanitary matters for transporting of preserved organs for transplantation.

Figure 11:
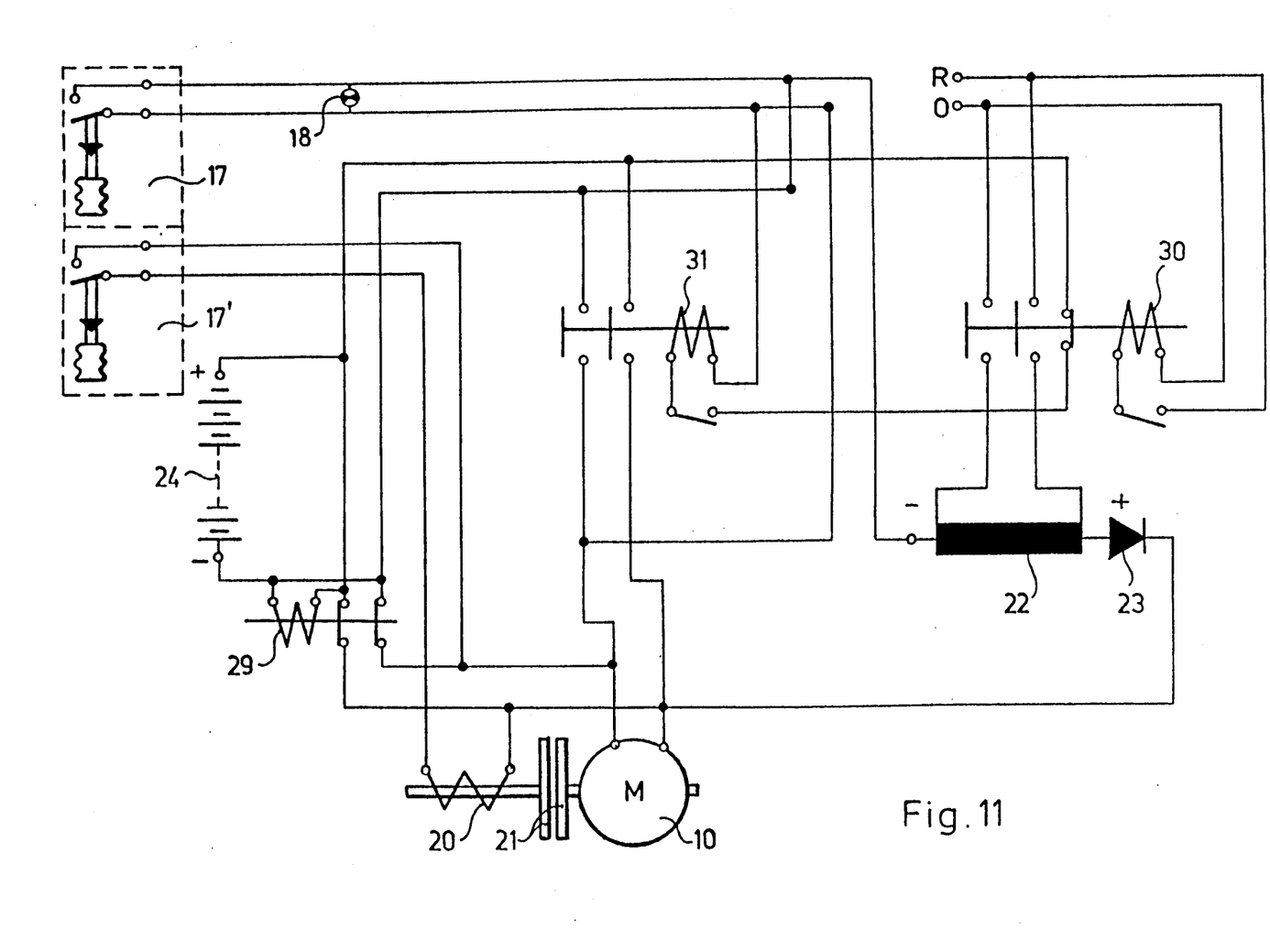
FIG. 11 is the electrical circuit diagram of an automatically controlled equipment for preservation of goods using the method complying with the invention, automatically switching over to battery operation in failure of mains supply.

FIG. 11 shows a further developed embodiment of the embodiment shown in FIG. 8, where the equipment is supplied from a D.C. motor 10 which is connected to the mains through transformer 22 and rectifier 23. During mains outages the equipment is automatically switched over to battery 24, the charging of which is ensured by contactor 29. On a mains outage, clutch 21 is operated through the interconnection of motor 10 and contactor 20 respectively, from battery 24. After recovery of the mains voltage the equipment is switched back to mains supply by contactor 30.

Figure 12:
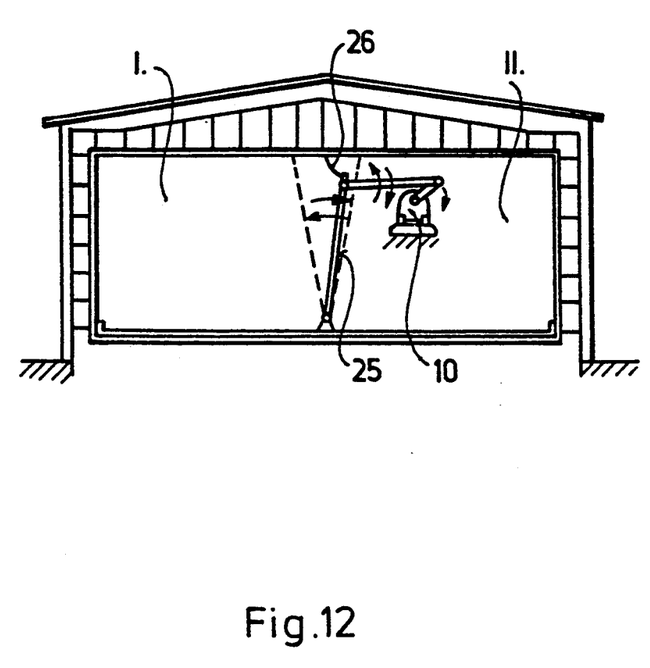
FIG. 12 shows the embodiment of the equipment suitable for preservation of goods by means of the method complying with the invention, realizing continuous variation of the pressure of gases filling up the hermetically sealed, larger storage space consisting of two chambers.

FIG. 12 shows a larger storage unit consisting of rooms forming chambers I and II for preserving products in compliance with the invention, where the fluctuating pressure variations of the gases filling up the closed spaces of storage units are brought about by partition wall 25 made up of a hermetically covered metallic frame moved by a crank drive integrally built with motor 10 causing the wall to assume two definite positions in succession, with a definite angle between said positions. The edge of wall 25 made up of said metallic frame is attached to the building by element 26 made of plastic or rubber ensuring thereby that the pressures developing in the two rooms do not deviate from their set values during the time of the required preservation period.

The temperature variations of the air spaces in the two rooms can be ensured, also in that case, by means of the methods similar to those already presented, i.e. by a basic cooling circuit. The principles of controlling the changes of pressure and temperature may be the same as those presented in FIGS. 1, 9, 10 and 11.

The control units of the various kinds of equipment proposed by the invention for the purpose of preservation are thermostats 17, 17'. The control system of the whole controlling regulation process however may incorporate e.g. time relays by which certain controll signals can effectively be influenced, or e.g. also computers may be added to the system opening the way toward optimizing the energy balance of the equipment during its operation or even to accomplish optimum service conditions e.g. by continuously controlling the temperature and pressure conditions in the preservation space.

Summing up the most important advantages of the method proposed according to our invention as follow:
a) the quality of products to be preserved (vegetables, meat, etc.) i.e. colour, flavour, hardness, etc. can be retained in its original state,
b) no substances harmful to the human organism are required to achieve fulfilment of preservation tasks.

We claim:

1. A process for preserving cellular perishable organic matter, which comprises
(a) placing the matter to be preserved into a closed space containing a gas;
(b) continuously substantially sinusoidally pulsing the gas pressure within said closed space at a predetermined frequency of at least 0.1 sec$^{-1}$, and a predetermined pressure pulse intensity under 8 kPa, from the time the matter to be preserved is placed into said closed space until it is removed therefrom;
(c) conducting said pulsing by varying said pressure intensity, wherein the higher the frequency of pulsing the lower the required variations of pressure intensity in said closed space;
wherein if said closed space is cooled to a temperature below 0° C., then the more the temperature in said closed space is reduced to below 0° C., the higher the required intensity of the pressure of said pulses, whereby the formation of disruptive freezing within said cellular matter is prevented; and
if the temperature within said closed space is cooled to below 0° C., then the pulsing of the pressure is started at a temperature not lower than 0° C., and the matter to be preserved being is removed from said closed space only at a temperature above 0° C.

2. The process of claim 1, wherein the gas in said closed space is air.

3. The process of claim 1, further comprising continuously substantially sinusoidally varying the temperature within said closed space to a minimum temperature of about −2° C.

4. The process of claim 3, wherein the temperature in said closed space is varied in a range between about +2° C. and about −2° C.

5. The process of claim 1, wherein the intensity of pulse pressure is between 97.5 and 102.5 kPa.

6. The process of claim 1, wherein the perishable organic matter is fruit, vegetable, edible meat, or a transplantable organ.

* * * * *